United States Patent [19]

Englund

[11] 4,338,809
[45] Jul. 13, 1982

[54] REMOTE READING, LIQUID PARAMETER MEASURING DEVICE AND IMPROVED PUMP

[76] Inventor: Richard L. Englund, 1831 127th Ave. Southeast, Bellevue, Wash. 98005

[21] Appl. No.: 161,657

[22] Filed: Jun. 23, 1980

[51] Int. Cl.³ ...................... G01F 25/00; G01F 23/14
[52] U.S. Cl. ........................................ 73/1 H; 73/302
[58] Field of Search ................. 73/302, 385, 747, 1 H; 116/227; 417/437

[56] References Cited

U.S. PATENT DOCUMENTS

| 2,012,511 | 8/1935 | Hubbard | 73/302 |
| 2,653,477 | 9/1953 | Hoskins | 73/302 |
| 3,307,397 | 3/1967 | Brown | 73/302 |
| 3,834,236 | 9/1974 | Durin | 73/302 |
| 4,072,053 | 2/1978 | Anderson | 73/747 |

FOREIGN PATENT DOCUMENTS 122847 8/1919 United Kingdom .................. 73/302

Primary Examiner—Charles A. Ruehl
Assistant Examiner—Denis E. Corr
Attorney, Agent, or Firm—Seed, Berry, Vernon & Baynham

[57] ABSTRACT

A hand-held, remote reading, liquid level measuring device, also suitable for measuring specific gravity or other parameters of the liquid, containing a supply of gauge liquid which is spill-proof in any position of the measuring device and with the measuring device becoming inoperative upon positions which would give excessive error in liquid level measurement readings. A unique combined pump check valve is also disclosed. A method is disclosed for accurately inserting a tube within the liquid to be measured so as to simulate the level measurement on a conventional dipstick.

11 Claims, 17 Drawing Figures

REMOTE READING, LIQUID PARAMETER MEASURING DEVICE AND IMPROVED PUMP

BACKGROUND OF THE INVENTION

1. Field of the Invention

This invention pertains to remote reading, liquid parameter measuring devices, particularly liquid levels in a reservoir, and to an air pump for use in this and other devices. More particularly, the invention is directed to a remote reading measuring device which contains a supply of gauge liquid that cannot leak from the device during shipment or in use.

2. Description of the Prior Art

Remote reading, liquid level measurement devices have been employed for many years. U.S. Pat. Nos. 2,012,511; 3,834,236 and 2,653,477 disclose structures which are intended to be permanently mounted in a location remote from the container having the liquid level to be measured. Generally, these devices are air-powered; that is, a pump provides a quantity of air to a tube immersed in the liquid to be measured and also to a manometric readout tube so that by supplying enough air to bubble out through the liquid to be measured, a readout of the level in the container is obtained on the sight tube of the manometric readout. When the specific gravity of the gauge fluid in the manometric tube is known and the height of the liquid level in the container above the bottom of the tube is known, specific gravity can also be determined.

There are several difficulties with the patented known measuring devices. Suitable provision is lacking for loss of the gauge fluid within the measuring device. Thus most of the prior art measuring devices are to be permanently mounted in a fixed, upright position so as to maintain both accuracy of reading and prevention of loss of the gauge liquid.

U.S. Pat. No. 3,307,397 is a more portable type of liquid level indicator which is intended to be secured to the dashboard of a vehicle. In this device, however, again no provision is adequately made for loss of the gauge liquid or errors when the angle of the device or, more specifically, the angle of the manometric sight tube in the device becomes too great so as to produce grossly inaccurate readings on the sight tube.

Another feature of the invention is directed to the problem that the manual pressurizing pumps for the prior art devices have involved expensive diaphragm pumps and check valves to provide the necessary pressurized air and venting, as is required for a manometric device.

Another feature of the invention is directed to the problem that none of the prior devices have an accurate, easy-to-follow technique for placing the tube within the liquid to be measured at an accurate distance below the level of the liquid in the container so as to accurately calibrate the sight tube in the manometric measuring device.

SUMMARY OF THE INVENTION

It is the first object of this invention to provide a remote reading, liquid level or other liquid parameter measuring device which can be loaded with gauge liquid during manufacture and which will not lose the gauge liquid during shipment or positioning of the device in any and all positions.

It is still another object of this invention to provide a remote reading, hand-held, portable, liquid level measuring device which reads only while in a position which will produce relatively accurate reading, but which is rendered inoperable in angles in excess of those providing accurate readings.

It is another object of this invention to provide an improved hand-held, remote reading, liquid level measuring device or combine devices which is easy to use and inexpensive to manufacture and maintain.

Basically, these objects are obtained by providing in the remote reading, liquid parameter measuring device means for manually creating a pneumatic pressure, a manometric measuring sight tube with indicia calibrated to measure the parameter of the liquid to be determined, a reservoir of gauge liquid connected to one end of the sight tube and means coupling the opposite end of the sight tube to a pressure atmosphere equal to the atmosphere over the measured liquid in the remote container, tube means coupling the gauge liquid reservoir and the measured liquid with said pressure-creating means, and means for preventing loss of the gauge liquid from within said gauge liquid reservoir due to movement in all directions of said measuring device in use. Stated differently, in its preferred embodiment, these objects are obtained by providing a remote reading, liquid level measuring device of the bubbler type with a manometric readout which is hand-held when operated and which can be hung up, laid down, shipped or stored away in any position of orientation, even though it contains a gauge liquid, without adverse effect on the operation of the device or loss of the contained liquid. It is particularly advantageous that the accurate amount of gauge liquid can be added at the factory because the liquid will not be lost during shipment or in use. Again in the preferred embodiment, the sight tube is rendered inoperative when it is tilted in any direction more than a predetermined angle by the provision of a funnel which has a downwardly diverging surface that becomes lifted out of the gauge liquid when angles are too excessive.

It is another object of this invention to provide a unique air pump check valve which is inexpensive to manufacture and easy to maintain.

Basically, this object of the invention is achieved by placing an elastically deformable cup loosely seated in a rigid chamber having a spaced circumferential wall around the cup such that depression of the cup will cause radial expansion to form a seal between the cup and the circumferential wall for pressurizing an air passage, but which when radially relaxed; that is, not depressed, forms an air leakage path to vent the cup. Thus the cup advantageously, with a single movable part, both pressurizes and vents in an inexpensive manner.

Still another object of the invention is to provide a method which accurately calibrates the sight gauge of a manometric measuring device.

Basically, this object is achieved in its broadest form by calibrating the sight tube to simulate the liquid level on a dipstick. In the preferred method this object is determined by removing the conventional dipstick, recording the liquid level "add" and "full" marks in the same relative positions as on the dipstick, permanently marking the "add" and "full" marks on the sight gauge in the same spacing as on the dipstick, inserting a pressure tube from the measuring device into the dipstick opening a slight distance beyond the "add" mark on the dipstick when the dipstick was inserted in the container and below the liquid level, locking the tube in this position on the container, taking a reading to compare the sight tube reading of liquid level with that previously recorded and then removing the tube and cutting off an amount equal to the difference between the two compared differences, and finally, relocking the tue in said container in a now-accurate position.

The advantage of simulating the dipstick reading is that it enables the sight tube to be accurately calibrated relative to the liquid level on the dipstick previously supplied by the engine or tank manufacturer. Thus there is no attempt to position the level tube or to use the sight gauge to tell the exact level of the liquid above the bottom of an engine, for example, or to determine the volume of the liquid which will vary infinitely in size and shape, but rather only to simulate the position of the dipstick in the engine. This offers the considerable advantage of relying on the accuracy of the dipstick indicia marks from the original manufacturer of the engine or container rather than having to determine liquid level absolutely in the container.

DESCRIPTION OF THE PREFERRED EMBODIMENTS

As best shown in FIGS. 1–4, the measuring device includes a hand-held pump and readout device 10 formed of a joined operating half 12 and a cover 14. While this embodiment will be described particularly as a hand-held, portable, remote reading, level measuring device of the bubbler type with a manometric readout, it should be understood that the device can be permanently, stationarily mounted or built into a piece of equipment during manufacture. An ideal application for this device is the measurement of oil level in automobile or boat engine crankcase from inside the operator station of the automobile or boat. In retrofit situations, it is not practical to permanently mount or "build in" a measuring device. Thus, for convenience of use and installation, such a measuring device should be located when not in use in an out-of-the-way location, such as in the glove box, or be hung beneath the dash. When the device is to be used to measure oil level, one can simply pick up the device in one hand, depress a button contained thereon, visually read the indicated oil level, and return the device to its stored location. It should also be understood that the device could also be used to measure fuel levels, water levels, transmission oil levels, and the like.

Figure 1:
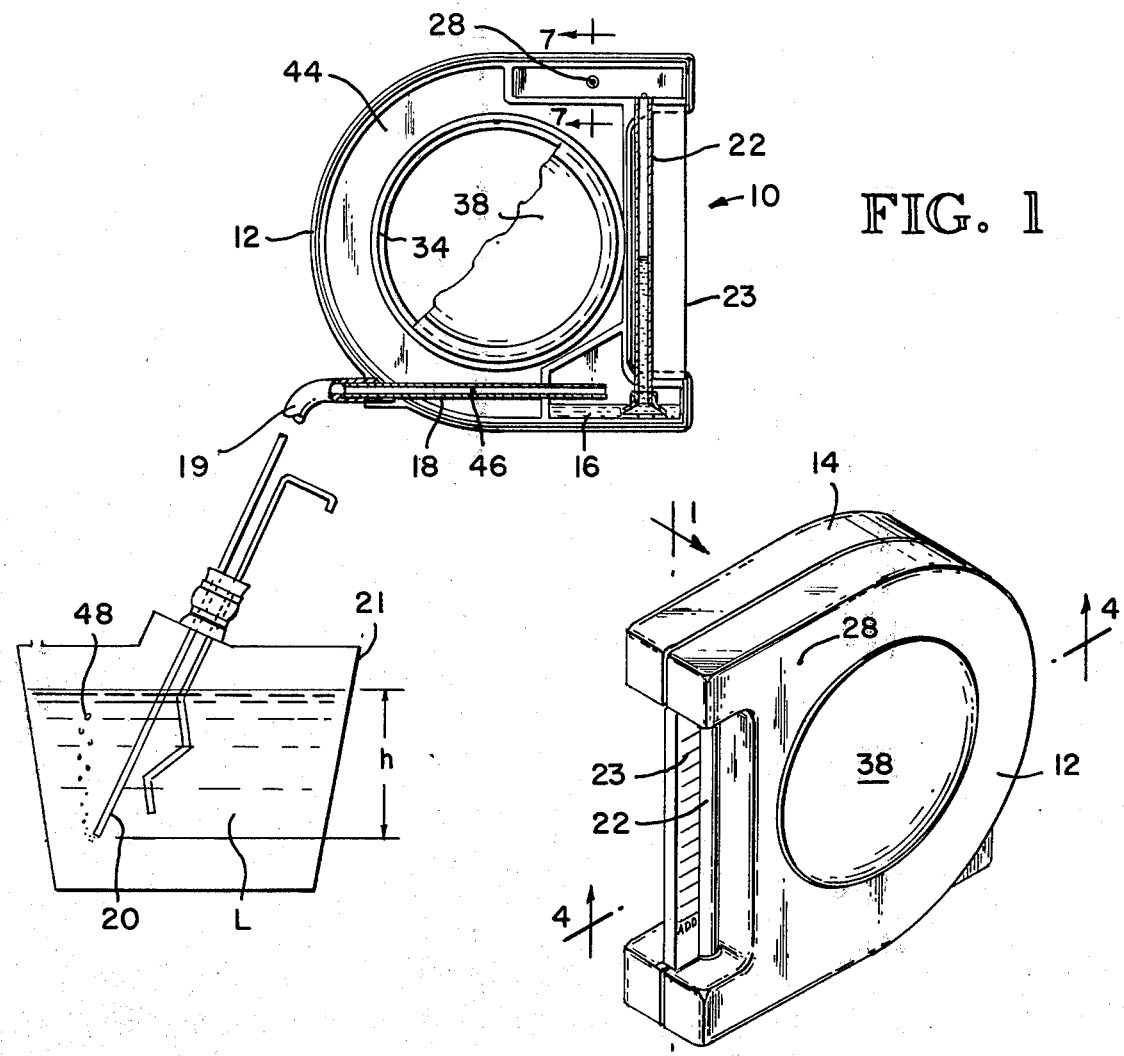
FIG. 1 is an operational schematic with parts broken away for clarity showing a liquid level measuring device in section operating to measure the liquid level in a remote container.
Figure 2:
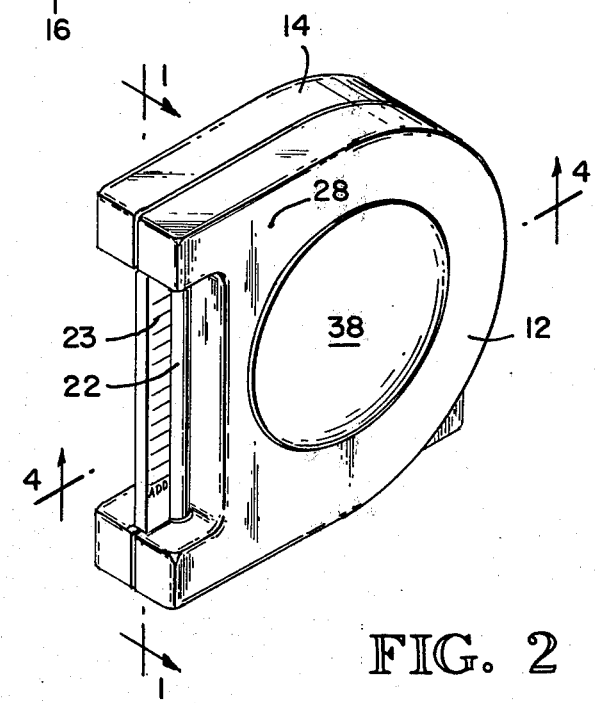
FIG. 2 is an isometric of the liquid level measuring device.
Figure 3:
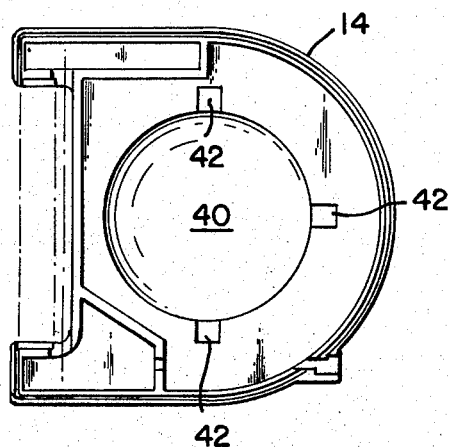
FIG. 3 is a vertical section taken thorugh the measuring device.
Figure 4:
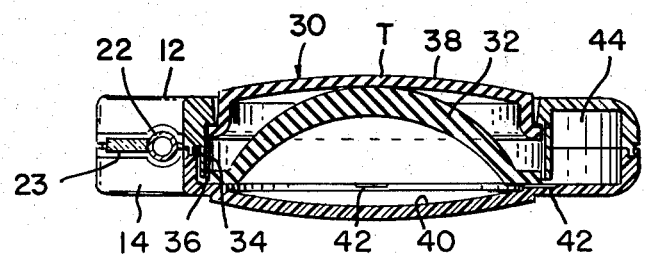
FIG. 4 is a horizontal section taken through the measuring device.
Figure 11:
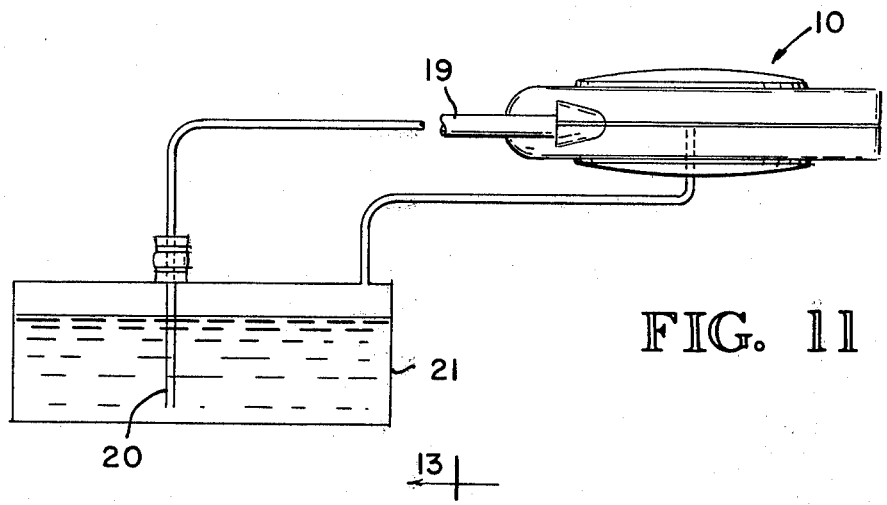
FIG. 11 illustrates a second embodiment, in which the container having the liquid level to be measured is at the same pressure as the top of the manometric sight tube.

The operational half 12 is best shown in FIG. 1 and includes gauge liquid reservoir 16 and an inlet tube 18 which couples the reservoir to a flexible tube 19 that terminates in a stiff tube 20 immersed in the liquid L to be measured in the engine or other container 21. The operational half also is provided with a manometric sight gauge 22 which, as best shown in FIG. 2, is provided with calibrated graduations or indicia 23. In the embodiment for measuring liquid level in an engine, these calibrations preferably will be the conventional "add" and "full" marks, as are found in an engine oil dipstick. A vent in the form of a raised tube 28 vents the top of the sight gauge 22 to the same atmosphere that exist above the level of liquid L in the container 21. It should be understood, and as best shown in FIG. 11, that this vent tube 28 can be coupled to the top of the container 21 in the event that the container 21 is pressurized so that the pressure existing above the manometric sight gauge 22 and the pressure above the liquid L in the container 21 are always equal.

The operational half is also provided with an air pump 30 which includes a chamber 31 in which is seated a cylindrical, elastomeric or flexible cup 32. The peripheral edge of the cup is spaced from a circumferential wall 34 to provide an expansion gap 36. The cup is depressed by a slidable, rigid button 38. The cover 12 is provided with a pressurizing chamber 40 having spaced recesses 42 which create air passages to a chamber 44 which communicates with the tube 18 via an orifice 46 in the tube 18. Pressurization occurs when the cup is depressed by radially expanding the cup against the circumferential wall 34 so that further depression of the cup pressurizes the chamber 44, thence through the tube 18 to simultaneously pressurize the reservoir 16 and the tube 19. Using the manometric bubbler concept, air bubbles 48 will begin to leave the bottom of the tube 20 when the static head of the vertical height of fluid L above the bottom of the tube 20 is proportional to the static head of gauge liquid in the sight tube 22. It should be understood that since the gauge liquid can be of a liquid density different than the liquid L, the height in the sight tube can be amplified or contracted proportionately to the vertical head in the container 21, depending upon the relative densities of the two liquids. Stated differently, the generated pressure causes; (a) the liquid to be expelled from the immersed end of the tube 20 and (b) the rise of gauge liquid into the manometer sight tube 22. As the generated pressure exceeds the static head pressure of the liquid L in which the tube 20 is immersed, bubbles of air emit from the end of tube 22. This bleeding-off of air limits the static or steady-state pressure in the pneumatic system to a value proportional to the immersion depth of the tube in the liquid L. Since the gauge liquid rises in response to this same system pressure, its height is proportional to the immersion depth h, or to the level of liquid L above the bottom of the tube 20. This proportionality is inverse to the ratio of the densities of the gauge liquid to the liquid L. If the densities are equal, the heights are equal.

Upon release of the force on the button 38, the elastic cup again returns to its original configuration, radially contracting away from the wall 34. This vents the pressure in the pneumatic system. The gauge liquid is prevented from being sucked up into the sight tube 22 because the system pressure is prevented from falling below atmospheric by two different features: (1) atmospheric air enters the system through vent 28 and (2) atmospheric air enters the air passage 44 as soon as the annular seal around the elastic cup 32 is broken by its radial expansion.

Figure 5:
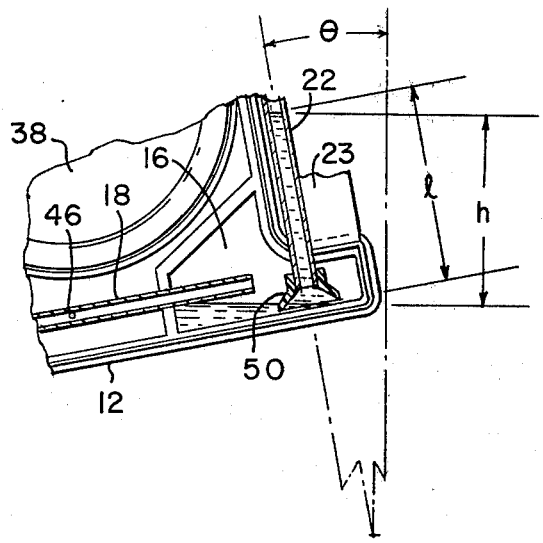
FIGS. 5–10 indicate portions of the device which schematically illustrate the spill-proof and the error prevention features of the invention.
Figure 6:
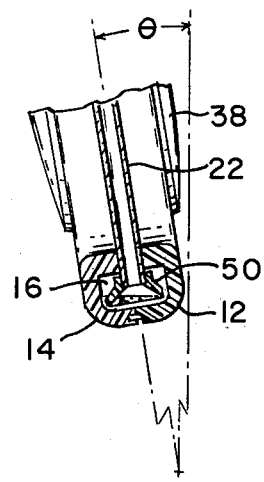

Considering that in the preferred embodiment, the measuring device is to be hand-held rather than permanently mounted, it should be noted that the vertical height of the gauge liquid may be different that the column length of the liquid in the sight tube 22. As best shown in FIGS. 5 and 6, the relationship of the vertical height $h = L \cos \theta$ or $L = h/\cos \theta$, where h equals the vertical height of the gauge liquid, L equals the column length of the gauge liquid along the sight tube 22, and $\theta$ equals the tilt angle.

Thus, if the device were tilted at an angle $\theta$ of 20 degrees, relative to the vertical, the indicated level L along the sight tube would be appproximately 6 percent higher than the true level h. To limit the inherent inaccuracy due to the tilting of the hand-held device, the gauge liquid enters the monometer tube or sight tube 22 through a cone or inverted funnel 50. This cone vents the tube if the tilt angle exceeds a specified limit. In FIGS. 5 and 6, the tube is shown tilted an angle $\theta$ greater than about 20 degrees and in an exaggerated form shows the gauge liquid in the reservoir 16 below the upper lip of the funnel so that in the illustrations of FIGS. 5 and 6, no reading will be possible as no liquid will be in the sight tube 22. These FIGS. 5 and 6 have been also used for purposes of illustrating the relationship of tilt angle to height and column length, even though it should be understood that in the illustration there would be no column length or L or vertical head h because these figures show the inoperative tilt angle. The limiting tilt angle, of course, is a function of the radius of the cone 50 and the depth of the gauge liquid as shown in FIGS. 5 and 6. If more accuracy than the maximum 6 percent error, which causes the sight tube to become inoperative, is desired, the cone diameter can be made larger so that the sight tube becomes vented at even smaller angles.

Figure 9:
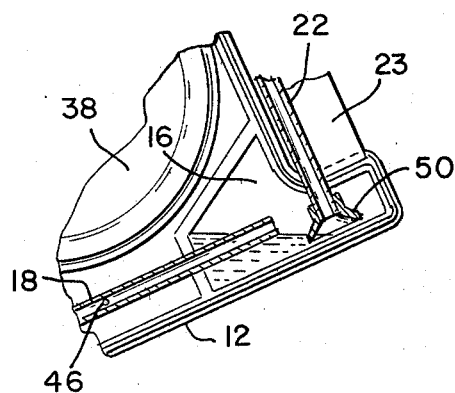
Figure 10:
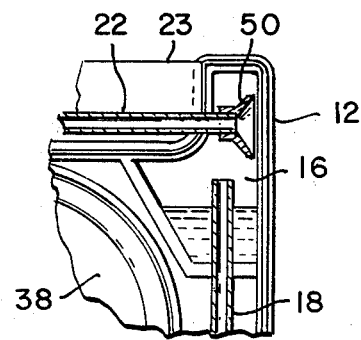

Of additional concern is the prevention of gauge liquid entering the pressure tube 18. Gauge liquid is prevented from entering the tube 18 due to the location and extent of protrusion of the tube 18 into the reservoir 16. As best shown in FIG. 1, the tube 18 is above the level of gauge liquid when the device is held horizontal. When the device is tilted into any angle, as shown in FIGS. 9 and 10, the protruding end of the tube 18 always remains above the level of the gauge liquid in the reservoir 16.

Figure 7:
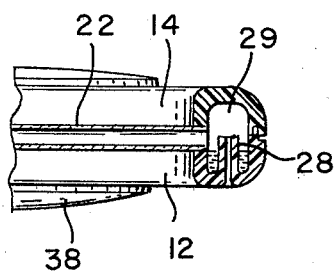
Figure 8:
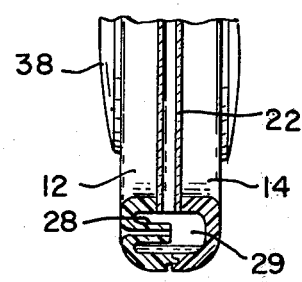

Similarly, the vent tube 28 is located as a protrusion such that any gauge liquid emitted from the upper end of the sight tube 22 cannot exit the vent port 28. This is accomplished by making the volume of the chamber 29 large enough such that the inlet to the port 28 will remain above the level of gauge liquid even if all of the gauge liquid is forced into the chamber 29. This could occur, for example, if the measured height h in the liquid L greatly exceeds the manometer tube 22 height. FIGS. 7 and 8 show that the relationship between the quantity of gauge liquid, the volume of the chamber 29, and the location of the inlet to the vent tube 28 is such that in any orientation of the measuring device, the gauge liquid level can never reach the inlet to the vent tube 28.

As described earlier, calibrating the indicia on the sight tube 22 to correspond to the actual liquid level in the container 21 is too difficult because the shape and size of the container may vary greatly between different applications. This invention uniquely uses the reliable dipstick calibration as is determined by the manufacturer at time of manufacture. Thus it is a unique feature of this invention to provide a method for calibrating the indicia on the sight tube 22 to correspond exactly with the indicia on the dipstick for any application or any container. This method is best shown in the illustrated steps from FIGS. 14-17.

Figure 15:
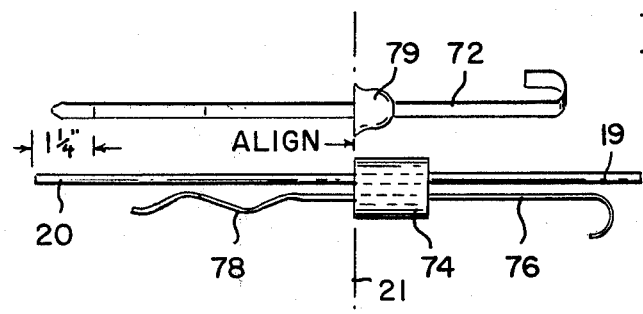

The first step is to make a piece of paper or the like 70 and record the "add," "full," and the oil level mark from the dipstick 72 of the engine or container. The tube 20 is adjustably seated in an elastomeric stopper or plug 74. A wire handle 76 having an undulating section 78 holds the inner end of the stopper firmly against the outside of the dip stick hole on the engine or container 21, as is shown in FIG. 15. That is, the bottom of the stopper is intended to be in the same position as the cap 79 on the dipstick 72.

Figure 16:
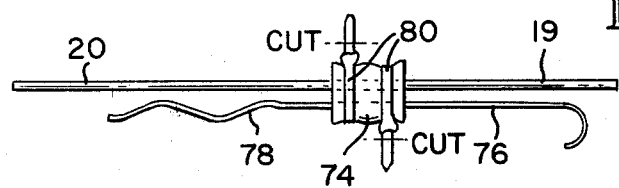
Figure 17:
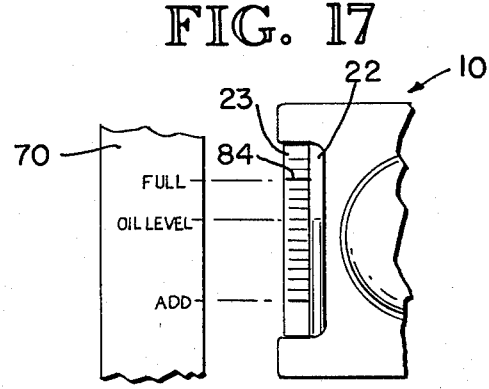

After these marks have been recorded on the paper 20, the tube 20 is inserted through the stopper 74 until the end of the tube extends approximately one and a quarter inches below the "add" line of the dipstick when the cap 79 and stopper 74 are aligned. Next, as best shown in FIG. 16, tie straps 80 are then tightened around the stopper to hold the handle 76 and tube 20 firmly in the stopper.

Next, the piece of paper 70 is held alongside the scale or indicia 23 and a piece of tape 84 added to represent the "full" line. It is located the same distance above the "add" line as on the paper. Holding the sight tube vertical, the button 38 is depressed three or four times, and an oil level will appear on the sight gauge. This oil level will probably be slightly greater than that marked on the paper. To correct this error, the plastic tube 20 is cut off at the lower end an amount equal to the error in the previous step. Then the procedure is repeated until the oil level actually appearing in the sight tube is equal to the oil level marked on the piece of paper when the "full" and "add" marks are aligned between the pape and the indicia or scale 23. If the oil level in the sight tube is too low, then the tube must be pushed further into the stopper.

The actual engine oil measurement for a vehicle engine is preferably done while the oil is warned so that it is not overly stiff. The engine should be off to assure an accurate reading. For best accuracy, the device should be held vertical. The button should be depressed slowly since the whole system responds more smoothly if the pressure change is not too fast. Using this measuring device, it can therefore be seen that convenient oil level indicator measurements can be determined quickly from within the car and without the operator getting soiled.

Figure 12:
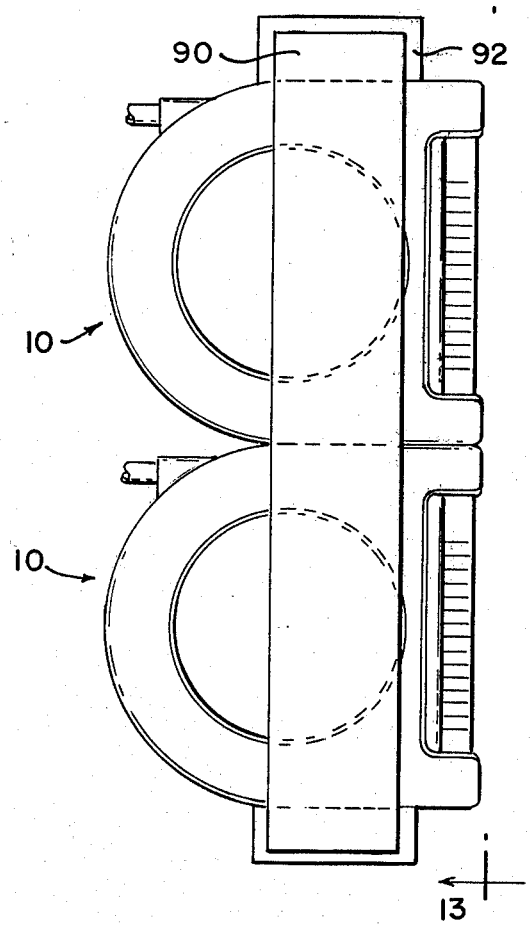
FIGS. 12 and 13 illustrate combination liquid level measuring devices which can be used to simultaneously or selectively measure two different liquid level measurements.
Figure 13:
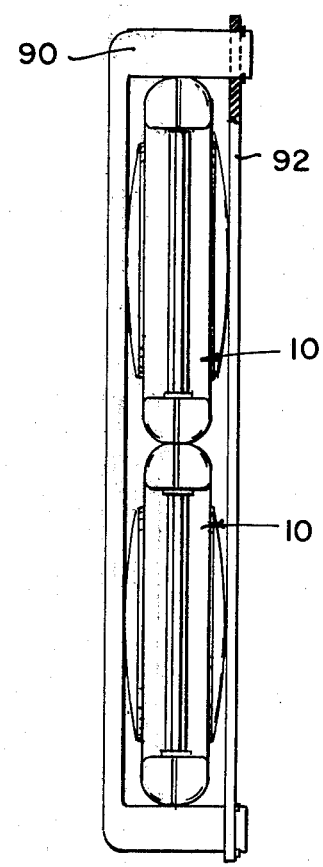
Figure 14:
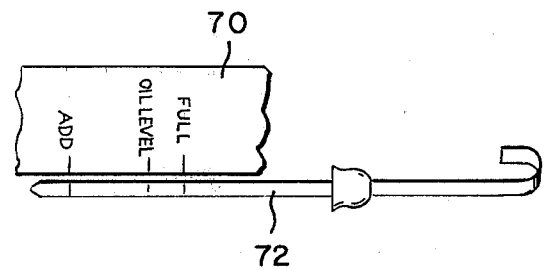
FIGS. 14–17 are operational schematics showing the method of calibrating the sight tube to simulate a dipstick according to the principles of the invention.

Another modification is shown in FIGS. 12 and 13. In this embodiment, two identical devices 10 are joined in a common case 90. The case is C-shaped and is slidably positioned in slots in a plate 92. With this device, two simultaneous readings can be taken from different engines, an engine and a fuel tank, two fuel tanks, etc. Thus the invention lends itself ideally to multiple liquid level measurement and would be particularly useful on a boat, which would have multiple engines, multiple fuel tanks, and the like.

While the preferred embodiment of the invention has been described with relation to automotive engines and container in general, it should be understood that its usefulness is quite broad, wherever a hand-held or even stationary, permanently mounted measurement device is to be used. Thus the invention should not be limited to the specific illustrations in the drawing, but rather modifications and variations will be apparent to one skilled in the art without departing from the principles herein.

I claim:

1. A hand-held, remote, reading, liquid parameter measuring device for measuring liquid in a container, comprising:
    means for manually creating a pneumatic pressure;
    a manometric measuring sight tube having spaced indicia calibrated to measure the parameter of the liquid to be determined;
    a reservoir of gauge liquid connected to a first end of said sight tube for movement into the sight tube upon pneumatic pressurization of the reservoir;
    means coupling the opposite second end of the sight tube to a pressure atmosphere equal to the atmosphere over the measured liquid in the container;
    pressure tube means coupling the gauge liquid reservoir and the measured liquid to said pressure-creating means;
    means for preventing loss of gauge liquid from said gauge liquid reservoir due to orientation in all directions of said measuring device in use; and
    means for rendering the sight tube inoperative when the device is tilted in all directions more than a predetermined angle to prevent substantial erroneous measurements.

2. The measuring device of claim 1, said pressure tube means including a gauge liquid end, said gauge liquid reservoir having a volume exceeding the volume of gauge liquid in the reservoir, said pressure tube means gauge liquid end having an opening positioned in the gauge liquid reservoir above the level of the gauge liquid in all positions of said measuring device for preventing loss of said gauge liquid.

3. The measuring device of claim 2, said means for rendering said sight tube inoperative including an outwardly converging, generally conical lip surrounding the lower first end of the sight tube, said lip being immersed in the gauge liquid when the measuring device is upright but opening the sight tube from the gauge liquid when tilted greater than said predetermined angle.

4. The measuring device of claim 3, wherein said predetermined angle is about 20 degrees in all directions.

5. A hand-held, remote, liquid level measuring device, comprising: a body, a chamber in said body having a circumferential containment wall, an elastically deformable cup in said chamber having a peripheral edge spaced from said containment wall, a seating surface for supporting said peripheral edge, a gauge liquid reservoir containing a volume of gauge liquid, air passage means beneath said seating surface for passing pressurized air to said gauge liquid reservoir, a container having a liquid whose level is to be measured, first pressure tube means connecting said air passage means to said container and having an open end at a predetermined location below said liquid level, a second pressure tube means connecting said air passage means and extending into the gauge liquid reservoir above the level of gauge liquid when the measuring device is upright, the volume of the gauge liquid reservoir being greater than said volume of gauge liquid, said second pressure tube means having an open end located within said gauge liquid reservoir to an extent that the level of gauge liquid is always below the open end regardless of the orientation of the device, a sight tube having a lower end and an upper end, liquid level indicia on said sight gauge, the upper end of said sight gauge joining a vent chamber, a port in said vent chamber located within said chamber at a position which is always above the level of gauge liquid regardless of the orientation of said measuring device, a conical, outwardly diverging lip on the lower end of said sight gauge, said lip being fully immersed in said gauge liquid when said device is upright but opening the lip when the measuring device is tilted in any angle over a set angularity, means for depressing said cup to pressurize said air passage means and produce a liquid level reading on said sight gauge proportional to the liquid level in said container, and means for attaching said device to a supporting structure.

6. The device of claim 5, including means for adjustably holding said first pressure tube means open end at said predetermined location in said container.

7. A one-way pneumatic pump comprising an elastically deformable convex cup loosely seated in a rigid chamber having a circumferential wall surrounding and spaced by an expansion gap from the peripheral edge of said cup, air passage means for connecting the chamber to a device to be pressurized, said cup being radially expandable when axially depressed to form a seal between the cup and the circumferential wall for pressurizing said air passage means but being radially relaxed when not depressed, forming an air leakage path through said gap, and means for depressinag said cup for creating said pressure.

8. The pump of claim 7, said rigid chamber including a seating ring for supporting the underside of said cup peripheral edge, said air passage means including at least one recess in said seating ring which remains unsealed during depression of said cup, and said means for depressing said cup including a rigid button loosely retained in said circumferential wall.

9. The method of locating and adjustably holding a pneumatic pressure tube having a lower end at a predetermined position beneath the level of a liquid in a container of the type provided with a liquid level dipstick showing "add" and "full" marks relative to a sight gauge on a manometric liquid level measurement device, comprising:
    removing the dipstick;
    recording the liquid level, "add" and "full" marks in the same relative positions as on the dipstick;
    permanently marking "add" and "full" marks on the sight gauge at the same spaced-apart distance as on the dipstick;
    inserting the lower end of the pressure tube from the measuring device into the dipstick opening of the container a slight distance beyond the "add" mark on the dipstick when the dipstick was inserted in the container;
    pressurizing the device and comparing the distance of the liquid level on the sight gauge from the "add" or "full" mark to the distance between liquid level and the corresponding "add" or "full" mark as recorded;

adjusting the location of the end of the tube in the container an amount equal to the difference between said two compared distances; and locking the tube in said container.

10. The method of locating and adjustably holding the lower end of a pneumatic pressure tube at a position beneath the level of a liquid in a container of the type provided with a liquid level dipstick showing "add" and "full" marks relative to a sight gauge on a manometric liquid level measurement device, such dipstick having a cap closing a dipstick opening, comprising:

removing the dipstick from the dipstick opening;

noting the liquid level, "add" and "full" marks in the same relative positions as on the dipstick;

permanently marking the distance between "add" and "full" marks on the sight gauge at the same spaced-apart distance as on the dipstick;

placing a stopper with the pressure tube therein against the dipstick opening;

adjusting the position of the lower end of the pressure tube from the stopper a prescribed short distance greater than the distance between the cap and the "add" mark on the dipstick;

pressurizing the device and comparing the distance of the liquid level on the sight gauge to the distance between liquid level and one of the "add" or "full" marks as noted;

adjusting the lower end of the tube relate to the stopper an amount equal to the difference between said two compared distances; and locking the tube in said stopper.

11. The method of claim 10 wherein said prescribed distance is about one to one and one-quarter inch.

* * * * *